(12) United States Patent
Savage et al.

(10) Patent No.: US 11,986,390 B2
(45) Date of Patent: May 21, 2024

(54) ATRAUMATIC COMPONENTS AND STRUCTURES FOR IMPLANTABLE DEVICES

(71) Applicant: Boston Scientific Scimed, Inc., Maple Grove, MN (US)

(72) Inventors: Padraig J. Savage, Santa Rosa, CA (US); Michael Lee, Santa Rosa, CA (US); Matthew Rust, Windsor, CA (US); Joshua Mark Inouye, Maple Grove, MN (US); Levi Wolterstorff, Saint Paul, MN (US); Graham Krumpelmann, Stillwater, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 125 days.

(21) Appl. No.: 17/554,760

(22) Filed: Dec. 17, 2021

(65) Prior Publication Data
US 2022/0192829 A1    Jun. 23, 2022

Related U.S. Application Data

(60) Provisional application No. 63/128,927, filed on Dec. 22, 2020.

(51) Int. Cl.
*A61F 2/24*    (2006.01)

(52) U.S. Cl.
CPC .......... *A61F 2/2445* (2013.01); *A61F 2/2442* (2013.01); *A61F 2/246* (2013.01); *A61F 2/2466* (2013.01)

(58) Field of Classification Search
CPC ...... A61F 2/2442; A61F 2/2445; A61F 2/246; A61F 2/2466
See application file for complete search history.

(56) References Cited

U.S. PATENT DOCUMENTS

| | | |
|---|---|---|
| 9,180,005 B1 | 11/2015 | Lashinski et al. |
| 9,192,471 B2 | 11/2015 | Bolling |
| 9,610,156 B2 | 4/2017 | Lashinski |
| 9,622,862 B2 | 4/2017 | Lashinski et al. |
| 9,795,480 B2 | 10/2017 | Bolling et al. |
| 9,848,983 B2 | 12/2017 | Lashinski et al. |
| 10,321,999 B2 | 6/2019 | Glenn et al. |
| 10,335,275 B2 | 6/2019 | Lashinski et al. |
| 10,548,731 B2 | 2/2020 | Lashinski et al. |
| 10,555,813 B2 | 2/2020 | Lashinski et al. |
| 2010/0249920 A1 | 9/2010 | Bolling et al. |

(Continued)

OTHER PUBLICATIONS

International Search Report and Written Opinion dated Mar. 22, 2022 for International Application No. PCT/US2021/064103.

*Primary Examiner* — William H Matthews
(74) *Attorney, Agent, or Firm* — Seager, Tufte & Wickhem, LLP

(57) ABSTRACT

Solutions for reducing irritation and/or trauma which may result upon contact of an implanted implantable device with tissue surrounding or adjacent to the implantable device. Various embodiments include features which allow a tangential or otherwise atraumatic contact of the implantable device with the tissue, in contrast with a sharper contact which may occur with prior art implantable devices. The broad principles are applicable to annuloplasty devices, and have other broader applications as well.

20 Claims, 16 Drawing Sheets

(56) References Cited

U.S. PATENT DOCUMENTS

| | | | |
|---|---|---|---|
| 2016/0015513 A1* | 1/2016 | Lashinski | A61M 25/0662 623/2.37 |
| 2016/0213500 A1 | 7/2016 | Beger et al. | |
| 2017/0135816 A1 | 5/2017 | Lashinski et al. | |
| 2018/0133003 A1* | 5/2018 | Levi | A61F 2/2412 |
| 2018/0228610 A1* | 8/2018 | Lashinski | A61F 2/2466 |

* cited by examiner

ATRAUMATIC COMPONENTS AND STRUCTURES FOR IMPLANTABLE DEVICES

PRIORITY

The present application is a non-provisional of, and claims the benefit of priority under 35 U.S.C. § 119 to, U.S. Provisional Application Ser. No. 63/128,927, filed Dec. 22, 2020, the disclosure of which is hereby incorporated herein by reference in its entirety for all purposes.

FIELD

The present disclosure relates generally to the field of implantable medical devices. More particularly, the present disclosure relates to components of implantable devices configured to reduce potential trauma which may be caused to tissue contacted by the implantable device once implanted in the body.

BACKGROUND

Various medical devices when implanted may contact tissue surrounding the implant site. Such contact may not be desirable and may lead to irritation and/or trauma to the contacted tissue. However, given differences in anatomy (and, particularly, sizes of anatomical structures) among various patients, and possible limitations to variations in sizes and relative dimensions of implantable devices, contact of at least a portion of an implantable device with tissue surrounding the implant site may not be avoidable. It would therefore be desirable to allow some contact between the implantable device and tissue adjacent the implantable device while reducing tissue irritation and/or trauma, and associated sequalae. Provision of atraumatic surfaces on an implantable device would allow an implantable device of a given size to be used in a greater number of patients with implant sites affording different degrees of clearance between the implantable device and tissue surrounding or adjacent the device when implanted.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with one aspect of the present disclosure, an implantable device includes a frame shiftable between a collapsed configuration and an expanded configuration, the frame having a distal end configured to be secured to tissue at an implant site, and a proximal end extending away from the distal end, the frame including a curved structure shielding the proximal end thereof from tissue surrounding the implant site.

In some embodiments, the frame includes a plurality of struts forming proximal apices along the proximal end of the frame, and the curved structure shields at least one proximal apex. Additionally or alternatively, the implantable device further includes a slider positioned over the at least one proximal apex, and the curved structure is on the slider. Additionally or alternatively, the curved structure is a rounded proximal end of the slider. In some embodiments, the implantable device further includes a slider screw engaging the slider to move the slider with respect to the struts to shift the frame between the collapsed configuration and the expanded configuration, the slider screw having a latch coupler on a proximal end thereof, and the curved structure shielding the latch coupler on the slider screw.

In some embodiments, the curved structure includes a rounded cap.

In some embodiments, the curved structure is a shield mounted on the at least one proximal apex.

In accordance with another aspect of the present disclosure, an implantable device includes a frame having an outer side and an inner side relative to a frame axis, a distal end configured to be secured to tissue at an implant site, and a proximal end configured to be coupled with a delivery/deployment device. The implantable device also includes at least one latch coupler configured to be coupled with a delivery/deployment device, and a curved structure shielding the at least one latch coupler from tissue surrounding the implant site.

In some embodiments, the implantable device further includes a slider mounted on a portion of the frame, and a slider screw engaging the slider to actuate the slider to shift the frame between a collapsed configuration and an expanded configuration, wherein the latch coupler is positioned on a proximal end of the slider screw. In some embodiments, the curved structure is a proximal end of the slider curved along an outer surface thereof and extending proximally towards a proximal end of the frame. In some embodiments, the curved structure is a proximal end of the slider curved from a side thereof extending transverse to the outer side of the frame, and extending towards a proximal end of the frame.

In some embodiments, the implantable device further includes at least one anchor on the distal end of the frame configured to secure the implantable device to tissue, and the latch coupler is positioned on a proximal end of the anchor.

In some embodiments, the at least one curved structure is a curved shield extending from the outer side of the frame towards the inner side of the frame to extend proximally over the at least one latch coupler. In some embodiments, the implantable device further includes a slider mounted on a portion of the frame, and a slider screw engaging the slider to actuate the slider to shift the frame between a collapsed configuration and an expanded configuration, the latch coupler being positioned on a proximal end of the slider screw; and the shield extending from the slider proximally over the latch coupler. In some embodiments, the implantable device further includes a slider mounted on a portion of the frame, and a slider screw engaging the slider to actuate the slider to shift the frame between a collapsed configuration and an expanded configuration, the latch coupler being positioned on a proximal end of the slider screw. and the shield being mounted on the frame proximal to the slider and slider screw and extends proximally over the latch coupler. In some embodiments, the curved shield includes first and second curved elements on either side of the latch coupler to allow access to the latch coupler by a delivery/deployment device therebetween. In some embodiments, the curved shield is flexible to allow access to the latch coupler by a delivery/deployment device therebetween.

In some embodiments, the curved structure includes a rounded cap extending over the latch coupler.

In yet another aspect of the present disclosure, an implantable annuloplasty device has a distal end configured to be implanted around a cardiac valve annulus and a proximal end configured to be coupled to a delivery/deployment device. The implantable annuloplasty device further includes a frame shiftable between a collapsed configuration and an expanded configuration to reconfigure the cardiac valve annulus, and a curved structure shielding the proximal end of the implantable annuloplasty device from the cardiac wall surrounding the cardiac valve annulus.

In some embodiments, the implantable annuloplasty device further includes a slider mounted on a portion of the frame, and a slider screw engaging the slider to actuate the slider to shift the frame between the collapsed configuration and the expanded configuration, the slider screw having a latch coupler on a proximal end thereof configured to be coupled with a latch on a delivery/deployment device, and the curved structure curving proximally over the latch coupler to shield the latch coupler from the cardiac wall surrounding the cardiac valve annulus.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows.

DETAILED DESCRIPTION

Figure 1:
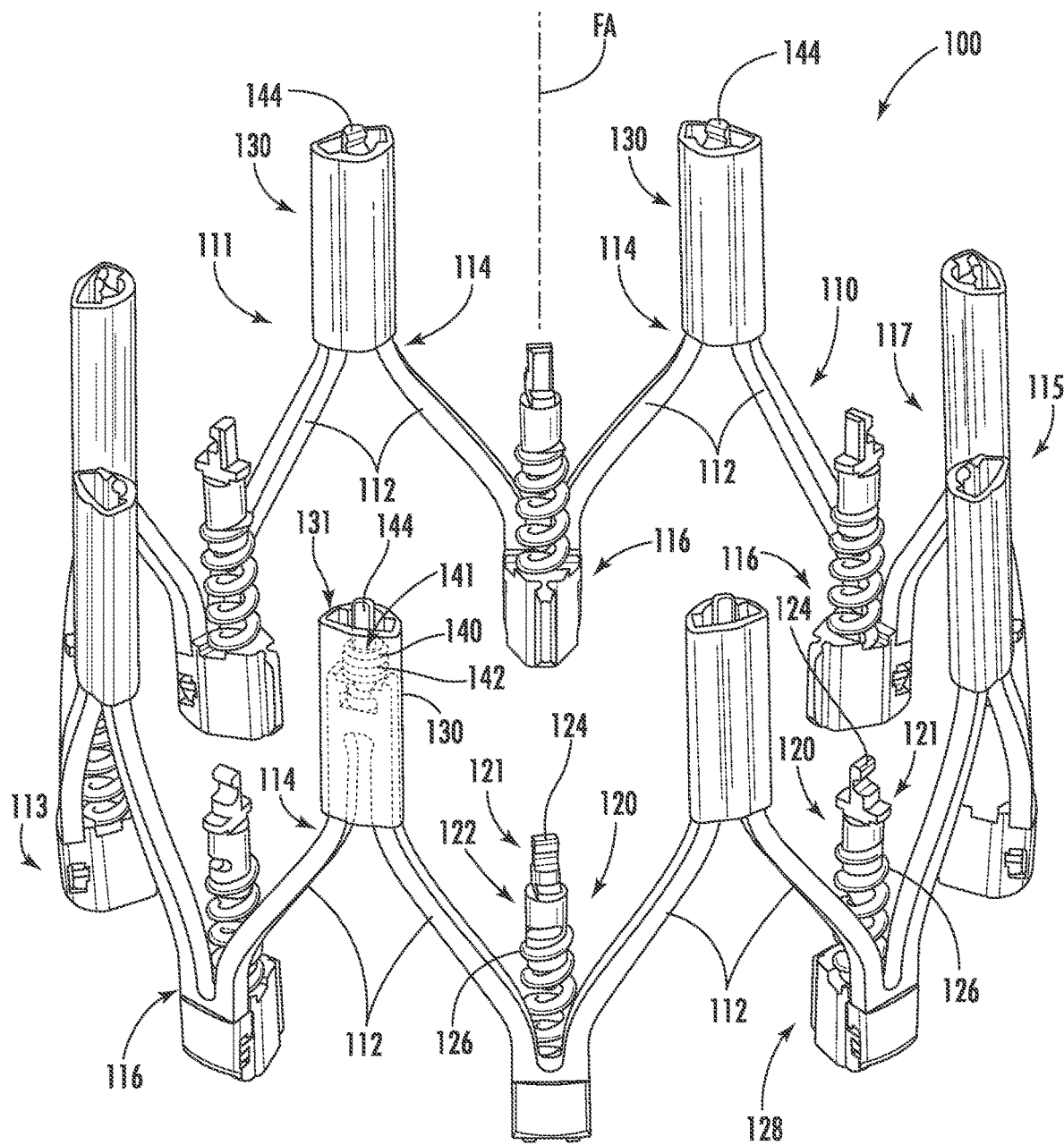
FIG. 1 is perspective view of an example of an implantable device formed in accordance with various principles of the present disclosure, with a slider illustrated in phantom to show a slider screw within the slider.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, "proximal" refers to the direction or location closest to the user (medical professional or clinician or technician or operator or physician, etc., such terms being used interchangeably without intent to limit or otherwise), etc., such as when using a device (e.g., introducing the device into a patient, or during implantation, positioning, or delivery), and "distal" refers to the direction or location furthest from the user, such as when using the device (e.g., introducing the device into a patient, or during implantation, positioning, or delivery). "Longitudinal" means extending along the longer or larger dimension of an element. "Central" means at least generally bisecting a center point, and a "central axis" means, with respect to an opening, a line that at least generally bisects a center point of the opening, extending longitudinally along the length of the opening when the opening comprises, for example, a tubular element, a strut, a channel, a cavity, or a bore.

The present disclosure presents various atraumatic concepts for features and structures of implantable devices, particularly devices which may come in close contact with body tissue or an organ. In accordance with various principles of the present disclosure, an implantable devices is designed to minimize or prevent potentially damaging contact of the device with tissue. Undesired contact of prior implantable devices (e.g., repeated contact, or contact of greater than a threshold force) with body tissue may injure the tissue. In some instances, such as in the case of contact of an implantable device with a cardiac wall, the damage may extend beyond the damage to the tissue. For instance, damage to the atrium wall may lead to atrium trauma, damage, and thrombus, which may result in even more serious conditions such as a major stroke, or even a fatal stroke. Various embodiments incorporating principles of the present disclosure include atraumatic structures that may allow a tangential contact of an implantable device rather than a sharp contact with tissue wall. More particularly, various principles of the present disclosure may be applied to mitigate and/or shield contact of a component of an implantable device which may in some circumstances be traumatic to tissue it contacts with more than a minimal amount of force, such as a screw head, or square edge or face of a component, or other non-rounded component. Various principles of the present disclosure thus may be applied to modify implantable devices to be less prone to undesirable contact with tissue, thereby preventing the damage cascade which may result from damaging contact, such as preventing thrombus. Contact which does occur is less prone to causing undesirable consequences, and thus expands the patient population treatable with implantable devices modified in accordance with various principles of the present disclosure. It will be appreciated that atraumatic structures include and are not limited to rounded corners and/or shields and/or chamfered edges, and the term atraumatic (and associated forms of such term) may be referenced alternately herein as curved, blunt, rounded, non-sharp, etc. (and associated forms of such terms), without intent to limit.

Various principles of the present disclosure may be applied to an implantable device implantable in tissue and capable of shifting between a collapsed configuration and an expanded configuration to reconfigure the tissue in which the device is implanted. In some embodiments, when the implantable device is in an expanded configuration components or surfaces thereof may come in contact with surrounding tissue. For instance, an annuloplasty device may be implanted in a cardiac valve annulus to repair and/or reconfigure the valve annulus by adjustment of one or more components thereof. In some embodiments, the annuloplasty device includes a frame and a cinch assembly configured to shift the frame between the collapsed configuration and the expanded configuration. It will be appreciated that the term shift (and conjugations and associated forms thereof) may being used interchangeably herein with such terms as adjust, move, or otherwise (and conjugations and associated forms thereof) without intent to limit. In some embodiments, the cinch assembly includes one or more cinch sleeves slidable with respect to the frame to move components of the frame relative to one another to allow expansion or contraction of the frame. It will be appreciated that the term contraction (and associated forms thereof) with respect to the frame may used interchangeably herein with terms such as retraction, collapse, cinching, and the like (and associated forms thereof), without intent to limit, to refer to moving the frame to a more compact configuration. The term sleeve (with or without the term "cinch") may be used interchangeably herein with terms such as slider or collar or nut without intent to limit, reference being made generally simply to sliders for the sake of convenience. The sliders may be individually adjusted to adjust different portions or sections of the frame to effect the desired adjustment of the configuration of the valve annulus such as to effect improved closure thereof.

In some embodiments, the slider is adjusted by rotation of a slider screw mounted on the frame, the slider and slider screw having mating threads. The slider screw may have a latch coupler configured to be coupled with a latch on a delivery/deployment device. In some embodiments, the delivery/deployment device comprises one or more flexible elongate members each with a latch on a distal end thereof engaging a latch coupler on a corresponding slider screw to rotate the slider screw. The slider screw may be mounted on the frame so as not to move axially with respect to the frame and the slider may be mounted on the frame so as not to rotate with respect to the frame so that rotation of the slider screw causes axial movement of the slider with respect to the frame. As the slider moves distally, the latch coupler of the slider screw may extend above the proximal end of the slider. Once the delivery/deployment device is removed from engagement with the implantable device, if the latch coupler or other surface of the slider screw is exposed, the device may contact the heart walls surrounding the device. For instance, as the heart beats, the nearby walls of the heart chamber in which the implantable device is positioned may contact a portion of the slider screw. The constant motion of the heart may cause undesirable interactions and irritations of the tissue contacting the slider screw.

In accordance with various principles of the present disclosure, one or more structures or features form a shield or barrier between various surfaces or portions or components of the implantable device and the tissue surrounding the implanted implantable device.

Various embodiments of atraumatically configured features and components of implantable devices will now be described with reference to examples illustrated in the accompanying drawings. Reference in this specification to "one embodiment," "an embodiment," "some embodiments", "other embodiments", etc. indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present invention is not limited to only the embodiments specifically described herein.

Turning now to the drawings, it will be appreciated that in the following description, elements or components similar among the various illustrated embodiments are generally designated with the same reference numbers increased by 100 and redundant description is omitted. Common features are identified by common reference elements and, for the sake of brevity, the descriptions of the common features are generally not repeated. For purposes of clarity, not all components having the same reference number are numbered. For the sake of brevity and convenience, and without intent to limit, common elements with common functions may be indicated with the same reference characters differing in value by 100, reference being made to previous descriptions of similar elements and operations.

An example of an implantable device 100 which may be formed in accordance with principles of the present disclosure is an implantable annuloplasty device, for custom reshaping of a heart valve (e.g., the mitral valve, or the tricuspid valve), such as illustrated in FIG. 1. It will be appreciated that various principles of the present disclosure are applicable to other forms and types of implantable devices, reference being made to an annuloplasty device as only one example of an implantable device to which principles of the present disclosure may be applied.

The example of an implantable device 100 illustrated in FIG. 1 includes a frame member 110 that may form a generally tubular shape extending about a frame axis FA. As used herein, the term "tubular" is to be understood to include circular as well as other rounded or otherwise closed shapes. As referenced herein, the frame axis FA is the axis relative to which the frame extends when expanded or contracted. In an embodiment of a frame 110 which is generally circular, the frame axis FA is a central longitudinal axis of the frame 110. The frame member 110 may assume various shapes, sizes, dimensions, configurations, etc. during different phases of deployment such as during pre-delivery, delivery, tissue engagement, anchoring, adjustment (e.g., cinching), etc. In the illustrated embodiment, the implantable device 100 may be a part of an implantable device delivery system configured to be delivered in a minimally invasive manner, such as for transluminal delivery to the heart. Accordingly, the implantable device 100 is delivered in a compact configuration (which may be referenced as a delivery configuration) with a proximal end 111 of the frame member 1100 coupled to a delivery/deployment device. It will be appreciated that the term compact may be used interchangeably herein with such terms as collapsed or compressed or simply unexpanded (such as with respect to the frame axis FA) without intent to limit. The implantable device 100 is expandable (such as in a direction away from the frame axis FA) into an expanded configuration for deployment, placement with respect to the treatment site (e.g., cardiac valve annulus), anchoring or securing to the treatment site, etc. The implantable device 100 may expand naturally (e.g., may be self-expandable), for example if the frame is formed of a shape memory or superelastic material (e.g., Nitinol) that is biased towards an expanded state. Alternatively, or additionally, the implantable device 100 may expand with assistance of an expansion device or mechanism, for example through the use of a force applied within the frame such as using an expandable deployment device (e.g., an inflatable balloon or the like). The frame member 110 may be configured to change shape, size, dimension, and/or configuration, such as to modify the shape, size, dimension, configuration, etc. of the valve annulus (or other structure) to which it is coupled.

In the illustrated embodiment, anchors 120 are provided at a distal end of the implantable device 100, such as at a distal end 113 of the frame 110, to anchor the implantable device 100 with respect to the treatment site. The anchors 120 may include an anchor shaft 122 with a latch coupler 124 at a proximal end 121 thereof, and an anchoring element 126 extending distally therefrom. The anchoring element 126 is configured to penetrate into tissue to anchor the implantable device 100 to the tissue, and may be helical as shown or in another appropriate configuration. The latch coupler 124 is configured to engage with a corresponding latch 1044 on a flexible elongate member 1042 of a delivery/deployment device (see FIG. 9 for a non-limiting example). An actuator 1040 (a generally tubular element, such as known or heretofore known in the art, the structure not being critical to the present disclosure, with one example being illustrated in FIG. 9) may extend over the latch coupler 124 and the latch 1044 to hold these elements in engagement (and thus hold the anchors 120 and implantable device 100 in engagement with the delivery/deployment device). The actuator 1040 may also be configured to engage with the anchor 120 to actuate the anchor 120 to advance or retract with respect to the implantable device 100 and the treatment site. As such, the actuator may alternately be referenced herein as a driver or controller (with or without the term "mechanism"), or a driver mechanism or control mechanism, without intent to limit. At least one of the anchors 120 may be a collar-based anchor advanceable through an anchor housing 128 such as in the form of a collar or sleeve or the like (as known or heretofore known in the art). It will be appreciated that other configurations of anchors and associated components thereof are within the scope and spirit of the present disclosure.

In the illustrated embodiments, one or more sliders 130 are provided to adjust the configuration of the frame 110. Each slider 130 preferably is adjustable independently of the other slider 130. Such adjustment results in adjustment of at least one of the size, shape, configuration, dimension, etc., of the frame 110 to affect at least one of the size, shape, configuration, dimension, etc., of the treatment site (such as to restore or correct the shape of a valve annulus for proper functioning or competency thereof). In the embodiment illustrated in FIG. 1, the sliders 130 may be advanced distally or retracted proximally with respect to the frame 110 upon rotation of a slider actuator screw 140 (referenced herein as a slider screw for the sake of simplicity and without intent to limit). The slider screw 140 has a threaded shaft 142 with external threads engaging corresponding internal threads 232 (see, e.g., FIG. 2) within the slider 130. Because the slider screw 140 is held axially with respect to the frame 110, and the slider 130 is held against rotation with respect to the frame 110, rotation of the slider screw 140 causes axial advancement of the slider 130 with respect to the slider screw 140. The slider screw 140 may be provided at a proximal end 141 thereof with a latch coupler 144 for engaging a latch of an actuator 1040 (see, e.g., FIG. 9) which rotates the slider screw 140. The actuator may be any known or heretofore known actuator in the art (the structure thereof not being critical to the present disclosure), and may be alternately referenced herein as a driver or controller (with or without the term "mechanism"), or a driver mechanism or control mechanism without intent to limit. It will be appreciated that engagement of a latch coupler 144 of the slider screw 140 with a delivery/deployment device may be similar to engagement of a latch coupler 124 of an anchor 120 with a delivery/deployment device, reference therefore being made above to such engagement for the sake of brevity.

In some embodiments, such as illustrated in FIG. 1, the frame 110 is formed from one or more struts 112 that may form all or part of the frame 110. The struts 112 may include elongated structural members formed of a metal alloy, a shape memory material, such as an alloy of nickel titanium or other metals, metal alloys, plastics, polymers, composites, other suitable materials, or combinations thereof. In one embodiment, the struts 112 may be formed from the same, monolithic piece of material (e.g., tube stock). Thus, reference to struts 112 may refer to different portions of the same, coextensive component. Alternatively, reference to struts 112 may refer to components that are formed separately and attached together (optionally permanently, such as by welding or soldering or other methods). In some embodiments, the struts 112 may be separate components that are detachably coupled to form proximal apices 114 and distal apices 116. Alternatively, if formed from a monolithic piece of material, the material may be cut or otherwise formed to define proximal apices 114 and distal apices 116. A slider 130 may be provided on one or more of the apices 114, 116 to adjust or shift the configuration of the frame 110. A slider 130 on a proximal apex 114 may be advanced distally towards the distal end 113 of the frame 110 to bring together the struts 112 forming such proximal apex 114 to collapse the frame 110 (reduce the overall width of the frame 110) towards the collapsed configuration. The slider 130 may be retracted proximally towards the proximal end 111 of the frame 110 to allow the struts 112 to move apart to allow the frame 110 to expand as described above. Adjustment or shifting of the configuration of the frame 110 may be achieved with the reverse movements of a slider 130 on a distal apex 116 (proximal movement to collapse the frame 110 and distal movement to allow expansion of the frame 110).

Further details of examples of frames, sliders, anchors, and further components and features thereof, and associated delivery devices and methods of use may be appreciated with reference to the following patents and patent applications, each of which is incorporated herein by reference in its entirety for all purposes: U.S. Pat. No. 9,180,005, issued Nov. 10, 2015, and titled "ADJUSTABLE ENDOLUMINAL MITRAL VALVE RING"; U.S. Pat. No. 10,335,275, issued Jul. 2, 2019, and titled "METHODS FOR DELIVERY OF HEART VALVE DEVICES USING INTRAVASCULAR ULTRASOUND IMAGING"; U.S. Pat. No. 9,848,983, issued Dec. 26, 2017, and titled "VALVE REPLACEMENT USING ROTATIONAL ANCHORS"; U.S. Pat. No. 10,555,813, issued Feb. 11, 2020, and titled "IMPLANTABLE DEVICE AND DELIVERY SYSTEM FOR RESHAPING A HEART VALVE ANNULUS"; U.S. Pat. No. 10,548,731, issued Feb. 4, 2020, and titled "IMPLANTABLE DEVICE AND DELIVERY SYSTEM FOR RESHAPING A HEART VALVE ANNULUS"; U.S. Pat. No. 9,192,471, issued Nov. 24, 2015, and titled "DEVICE FOR TRANSLUMENAL RESHAPING OF A MITRAL VALVE ANNULUS"; U.S. Patent Application Publication No. 2010/0249920, published Sep. 30, 2010, and titled "DEVICE FOR TRANSLUMENAL RESHAPING OF A MITRAL VALVE ANNULUS"; U.S. Pat. No. 9,795,480, issued Oct. 24, 2017, and titled "RECONFIGURING TISSUE FEATURES OF A HEART ANNULUS"; U.S. Pat. No. 9,610,156, issued Apr. 4, 2017, and titled "MITRAL VALVE INVERSION PROSTHESES"; and/or U.S. Pat. No. 10,321,999, issued Jun. 18, 2019, and titled "SYSTEMS AND METHODS FOR RESHAPING A HEART VALVE". Thus, the description of particular features and functionalities herein is not meant to exclude other features and functionalities, such as those described in the references incorporated herein by reference or others within the scope of the development.

Various components of prior art implantable devices 100 may, when the implantable device 100 is implanted, contact tissue surrounding the treatment site. As may be appreciated, it is desirable for various surfaces and features along the exterior 115 (which may be alternately referenced herein, without intent to limit, as an outer side) of the frame 110 to be shaped to be atraumatic so as not to irritate and/or traumatize tissue surrounding the treatment site (which may result in thrombus and/or other sequalae). Some features or components, such as latch couplers 124, 144, may present a corner which may not be able to be sufficiently atraumatically shaped to avoid irritating tissue which it contacts. An anchor 120 at a distal end 113 of the frame 110 may be positioned along the interior 117 (which may be alternately referenced herein, without intent to limit, as an inner side) of the frame 110 to minimize contact of components associated with the anchor 120, including the anchor latch coupler 124, with surrounding tissue. As such, the latch couplers 124 on the proximal ends 121 of the anchor 120 may be shielded by the frame 110 of the implantable device 100 from contacting tissue. However, it generally is more challenging to shield the latch coupler 144 of the slider screw 140 from tissue surrounding the treatment site, particularly when the sliders 130 and associated slider screws 140 are mounted on a proximal end 111 of the frame 110.

In accordance with various principles of the present disclosure, various structures and features of an implantable device 100 are provided herein with atraumatic surfaces for potential contact with tissue surrounding the implantable device 100. Such surfaces may be rounded or otherwise provide tangential contact with tissue in contrast with corners or other surfaces which may be considered in the field to be potentially more traumatic. For instance, a radius of curvature of a curved surface or the dimension of chamfer could be greater than approximately 0.005" (0.127 mm) at most approximately 0.1" (2.54 mm) (including increments of 0.01 mm therebetween). Although the embodiments described herein and illustrated in the accompanying drawings are with respect to sliders 130, 230, 330, 430, 530, 630, 730, 830, 934, and latch couplers 124 associated therewith, it will be appreciated that similar principles may be applied to latch couplers 144 of anchors 120, and other components associated with anchor 120, as well.

Figure 2:
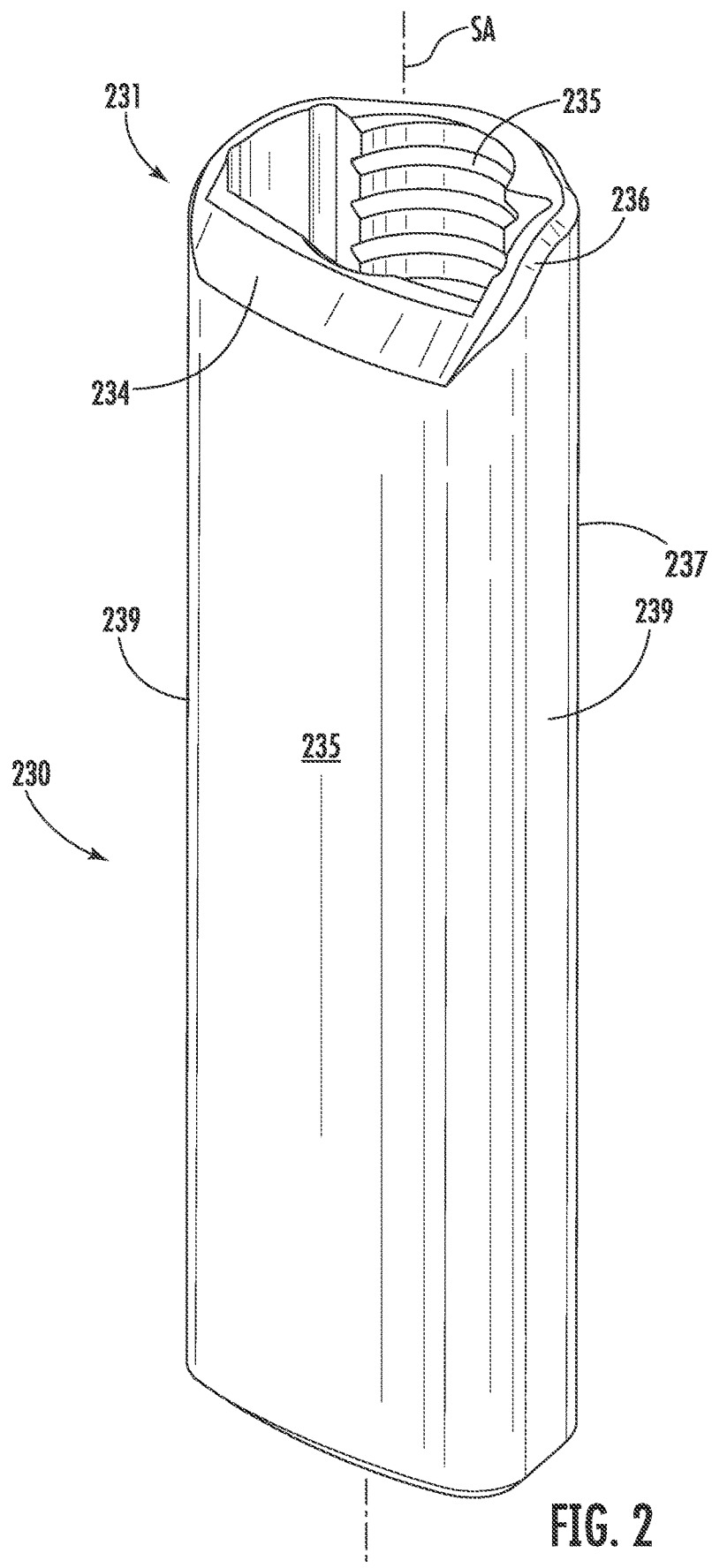
FIG. 2 is a front and proximal perspective view of an example of an embodiment of an atraumatic structure formed in accordance with various principles of the present disclosure.
Figure 3:
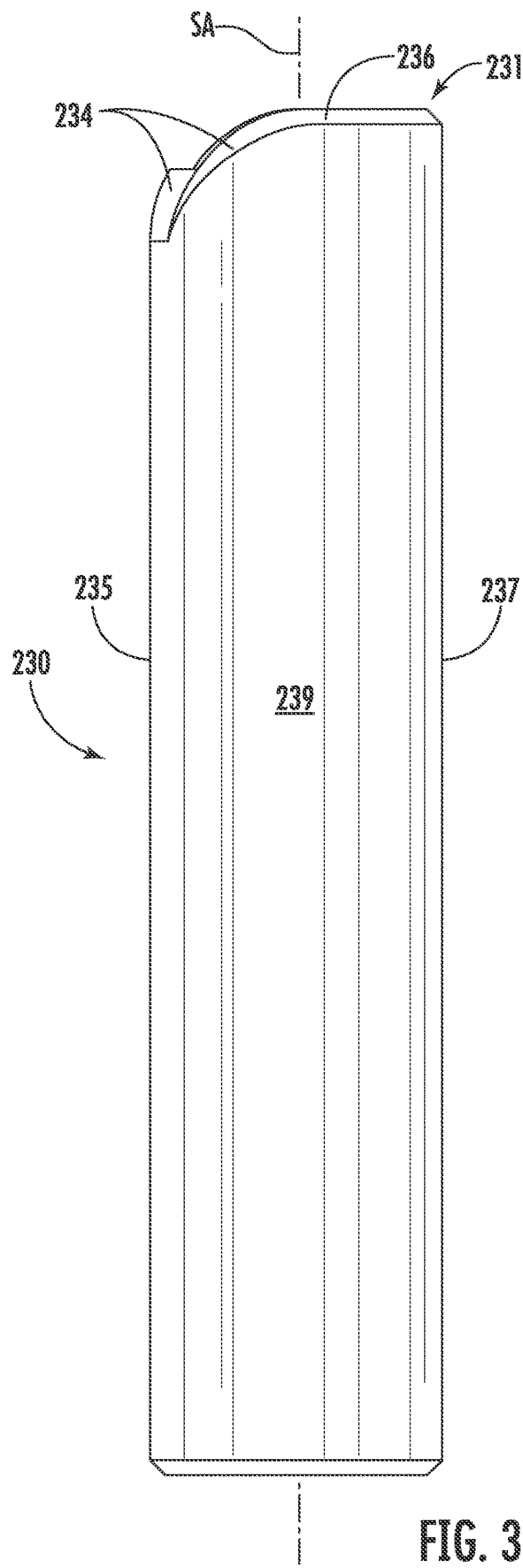
FIG. 3 is a side elevational view of an atraumatic structure as in FIG. 2.
Figure 4:
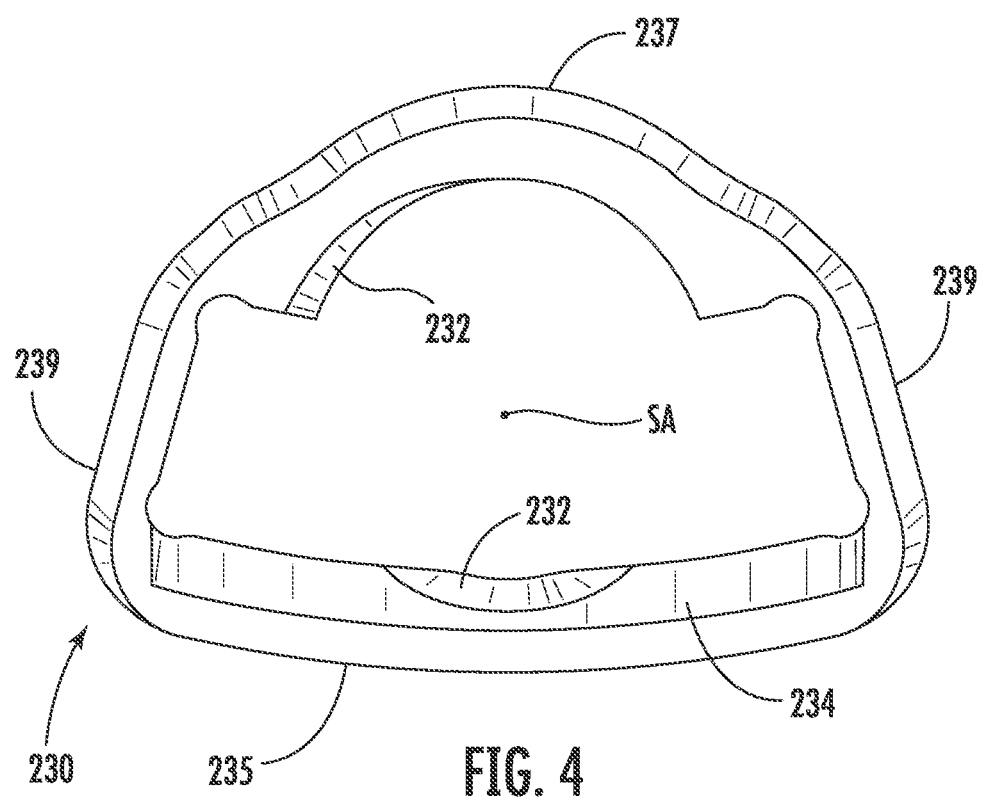
FIG. 4 is a proximal end view of an atraumatic structure as in FIG. 2 or FIG. 3.

In the embodiment illustrated in FIGS. 2-4, a slider 230 formed in accordance with various principles of the present disclosure has a curved transition surface 234 from the outer surface 235 thereof (which may also be referenced herein as the front surface without intent to limit) to the proximal end 231 thereof. The curved transition surface 234 may have a radius of curvature of at least approximately ½ to the full distance between the front or outer surface 235 to the back or inner surface 237 of the slider 230. It will be appreciated that the curvature need not be constant. Moreover, it will be appreciated, such as with reference to FIG. 2 and FIG. 3, that the proximal ends of the side surfaces 239 (extending transverse to and between the outer surface 235 and the inner surface 237), and/or any other edges and/or meeting of surfaces, may have a chamfer 236 or otherwise somewhat rounded surface (e.g., break edges, or other geometry of less than 90°) as well. The outer surface 235 of the slider 230 of FIGS. 2-4 thus may be considered to form a curved structure configured to contact tissue surrounding the implantable device 100 (such as the atrium wall in some embodiments) atraumatically. Also in contrast with prior sliders, the sliders 230 of FIGS. 2-4 may be longer (in a direction along the longitudinal axis SA) to better shield surrounding tissue from a latch coupler 124 of a slider screw 140 (e.g., as in FIG. 1) positioned therein.

In various prior art sliders, the outer surface of the slider may have a bulge extending longitudinally along the slider longitudinal axis SA (and generally substantially equidistant from the sides of the slider) to accommodate a slider screw 140 (e.g., as in FIG. 1). In accordance with various aspects of the present disclosure, in some embodiments, such as illustrated in FIG. 2 and FIG. 4, the outer surface 235 of a slider 230 has a relatively constant curvature with a bulge in the center region (substantially equidistant from the side surfaces 239). The slider 230 illustrated in FIGS. 2 and 4 provides sufficient wall surface for the internal threads 232 within the slider 230 which made with the threaded shaft 142 of the slider screw 140, yet presents a more gently curved outer surface 235 than in prior art sliders. Such smoothly curved or contoured outer surface 235 may be formed such as by extruding material out on either side of the slider wall in which the threads 232 are provided. The outer surface 235 may be considered to have additional surface area as compared with prior art sliders. As such, the outer surfaces 235 of the sliders 230 of FIGS. 2-4 provide an increase in focal area of pressure against surrounding tissue, and a concurrent reduction in any potential trauma such pressure may produce.

Figure 5:
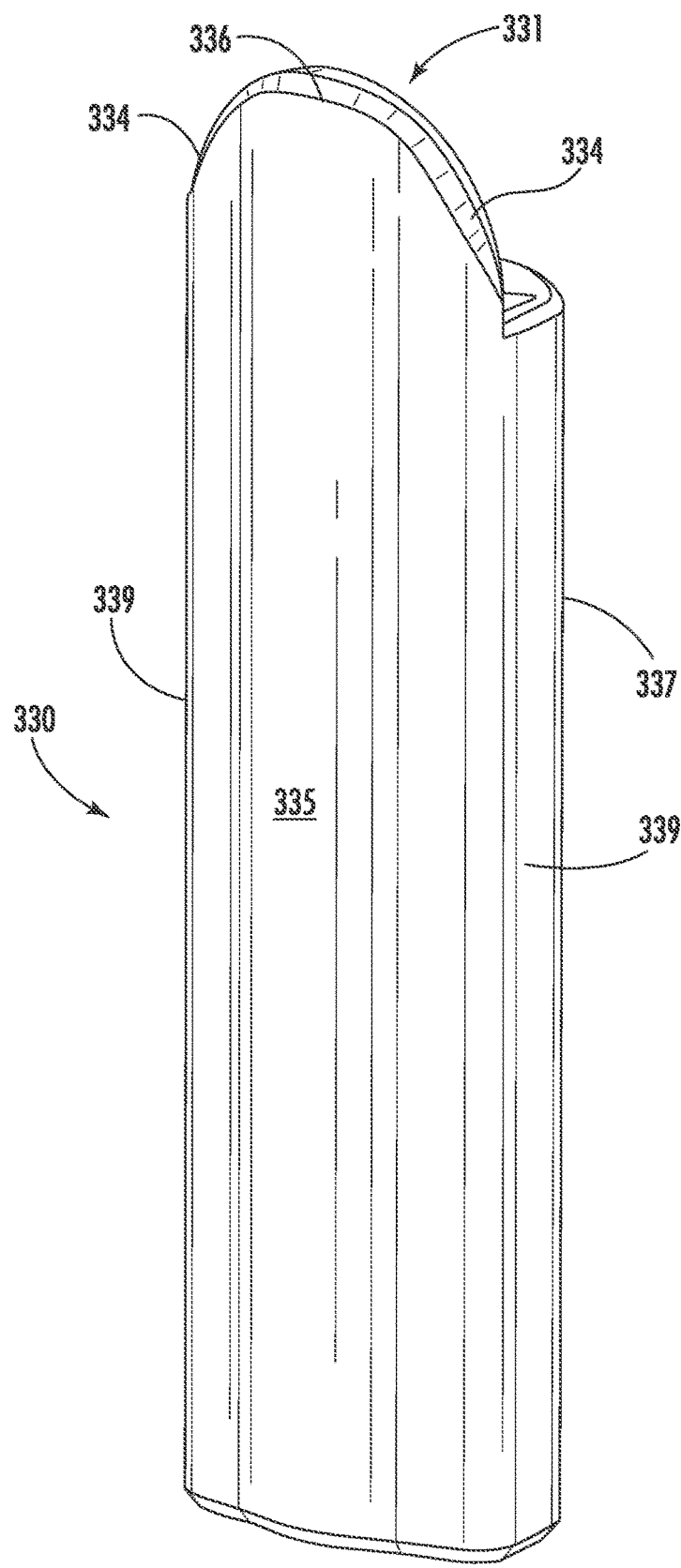
FIG. 5 is a front and proximal perspective view of an example of an embodiment of an atraumatic structure formed in accordance with various principles of the present disclosure.
Figure 6:
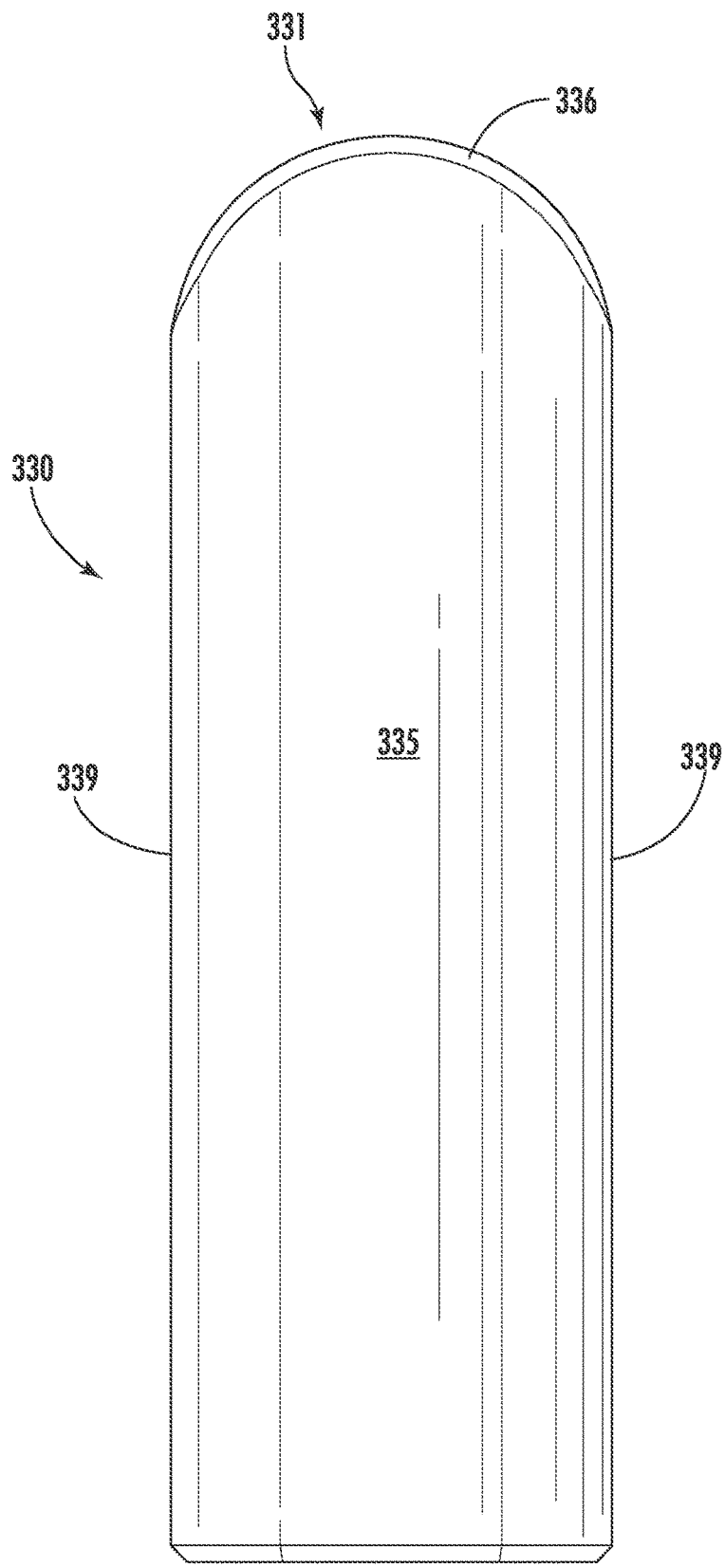
FIG. 6 is a front elevational view of an atraumatic structure as in FIG. 5.
Figure 7:
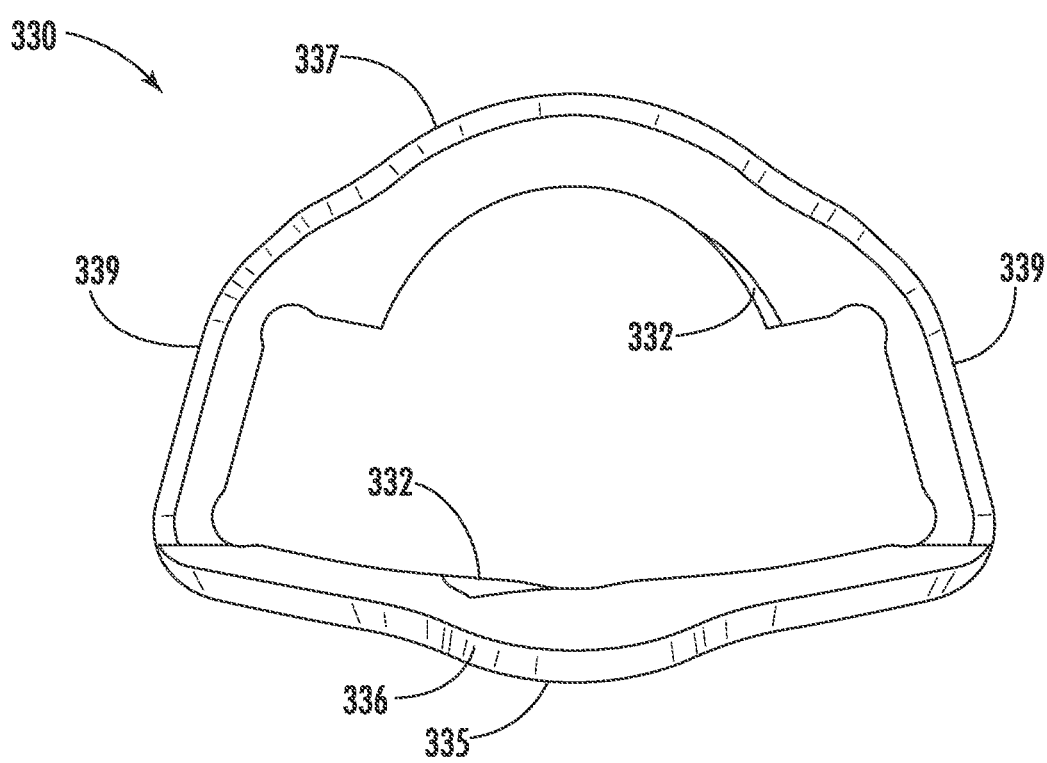
FIG. 7 is a proximal end view of an atraumatic structure as in FIG. 5 or FIG. 6.

Alternatively or additionally, and as illustrated in FIG. 5, FIG. 6, and FIG. 7, a slider 330 formed in accordance with various principles of the present disclosure has rounded transition surfaces 334 from the outer surface 335 thereof to either side surface 339 along the proximal end 331 of the slider 330. The rounded transition surface 334 may have a radius of curvature of at least approximately ¼ to at most approximately ½ the full distance (width) between the side surfaces 339 of the slider 330. It will be appreciated that the curvature need not be constant. For instance, the middle portion (spaced from each of the side surfaces 339, such as equidistantly spaced) may be somewhat straight (e.g., substantially perpendicular to the longitudinal axis SA) and the side regions (on either side of the middle portion) may have radii of curvature approximately ¼ the full distance between the opposed side surfaces 339 of the slider. It will be appreciated that the edge of the outer surface 335 from the front (outer surface 335) to the back (towards the inner surface 337) of the slider 330, and/or any other edges and/or meeting of surfaces, may be curved or may have a chamfer 336 or otherwise may be somewhat rounded (e.g., break edges, or other geometry of less than 90°) as well. The outer surface 335 of the slider 330 of FIGS. 5-7 thus may be considered to form a curved structure configured to contact tissue surrounding the implantable device 100 (such as the atrium wall in some embodiments) atraumatically. Also in contrast with prior sliders, the sliders 330 of FIGS. 5-7 may be longer (in a direction along the longitudinal axis SA) to better shield surrounding tissue from a latch coupler 124 of a slider screw 140 (e.g., as in FIG. 1) positioned therein.

As may be seen in FIG. 7, the walls of the slider 330 are sufficiently thick for threads 332 to be formed in the interior of the slider 330 to engage with a threaded shaft 142 of a slider screw 140 (e.g., as in FIG. 1). A bulge at the middle of the outer surface 335 extending along the longitudinal axis SA may be provided, or a substantially constant curvature may be provided along the outer surface 335 extending between the side surfaces 339 (as in the embodiment of FIGS. 2-4).

Figure 8:
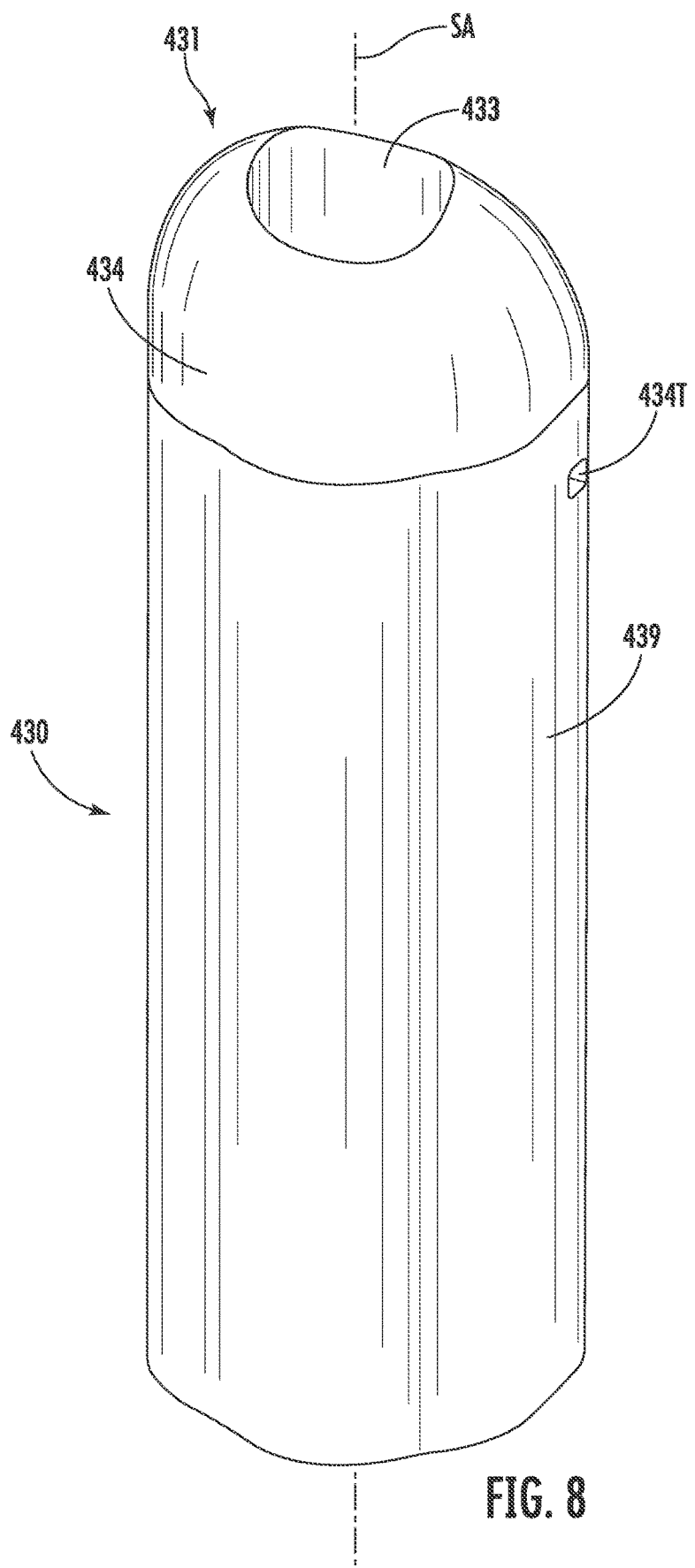
FIG. 8 is a front and proximal perspective view of an example of an embodiment of an atraumatic structure formed in accordance with various principles of the present disclosure.
Figure 9:
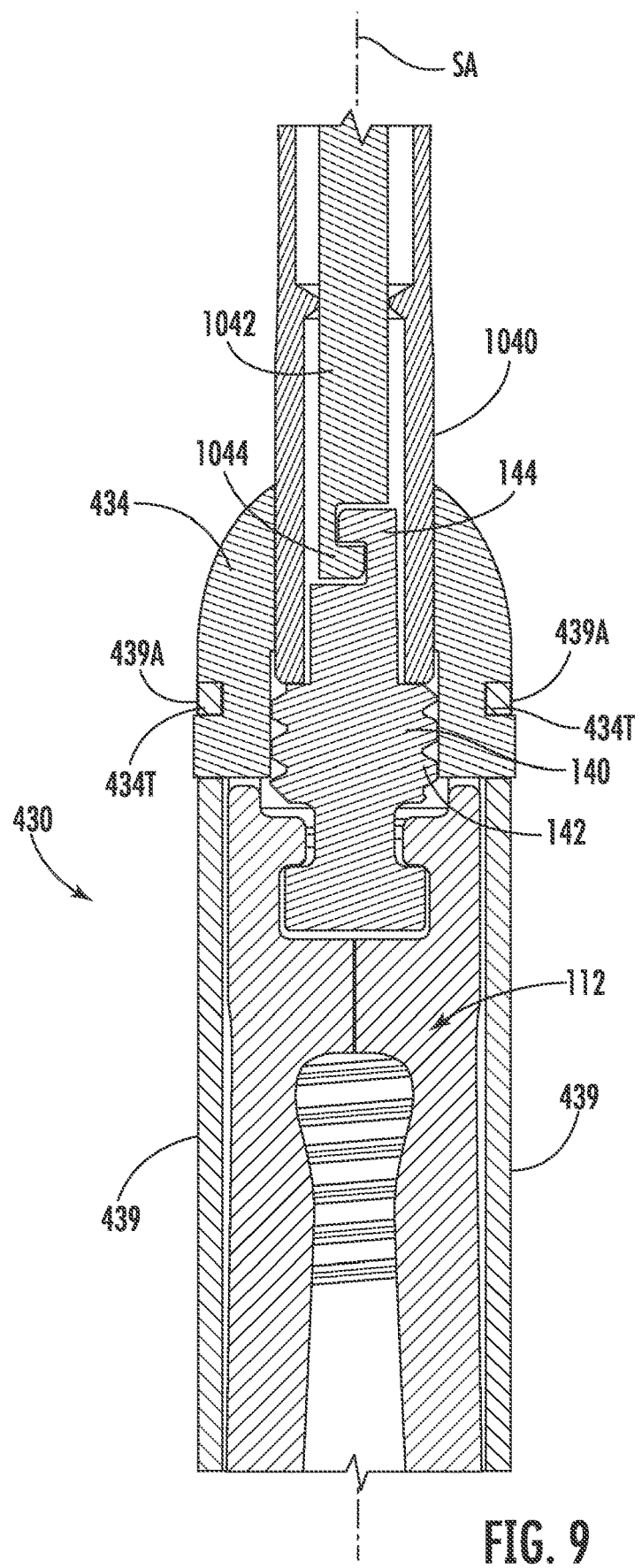
FIG. 9 is a cross-sectional view of the atraumatic structure of FIG. 8 along line IX-IX.

Atraumatic structures, such as structures associated with sliders, may be provided in other manners without departing from the scope and spirit of the present disclosure. For instance, a slider 430 may be provided with a rounded cap 434 over the proximal end 431 of the slider 430, such as illustrated in FIG. 8 and FIG. 9. As may be appreciated with reference to FIG. 8, the rounded cap 434 presents a slider 430 with an overall curved substantially atraumatic surface along the proximal end 431 of the slider 430. The rounded cap 434 may have a longitudinal aperture 433 extending along the longitudinal axis SA of the slider 330 to permit access therethrough to an actuator 1040 for engaging and actuating the latch coupler 124 of a slider screw 140 positioned within the slider 430 and engaged with a latch 1044 at the distal end of a flexible elongate member 1042, as illustrated in FIG. 9. The rounded cap 334 also covers the proximal apex 114 of the frame 110 of the implantable device 100 (such elements shown in greater detail in FIG. 1), further protecting surrounding tissue from contact with surfaces of the implantable device 100 which may not be as rounded as would otherwise be desirable to reduce trauma to surrounding tissue. The rounded cap 434 may be formed of a material similar to that of the slider 430 (e.g., stainless steel), or of a more flexible material such as an elastomeric material (e.g., silicone). In some embodiments, the rounded cap 434 may include resilient extensions or tabs 434T to fit in corresponding apertures 439A in the side walls 439 of the slider 430 to hold the rounded cap 434 in place with respect to the slider 430.

Variations of other curved structures, such as caps or shields or cages or the like (such terms may be used interchangeably herein without intent to limit), which may be provided in connection with an implantable device (in the illustrated embodiments, associated with sliders, but not necessarily so limited) are illustrated in FIGS. 10-15.

Figure 10:
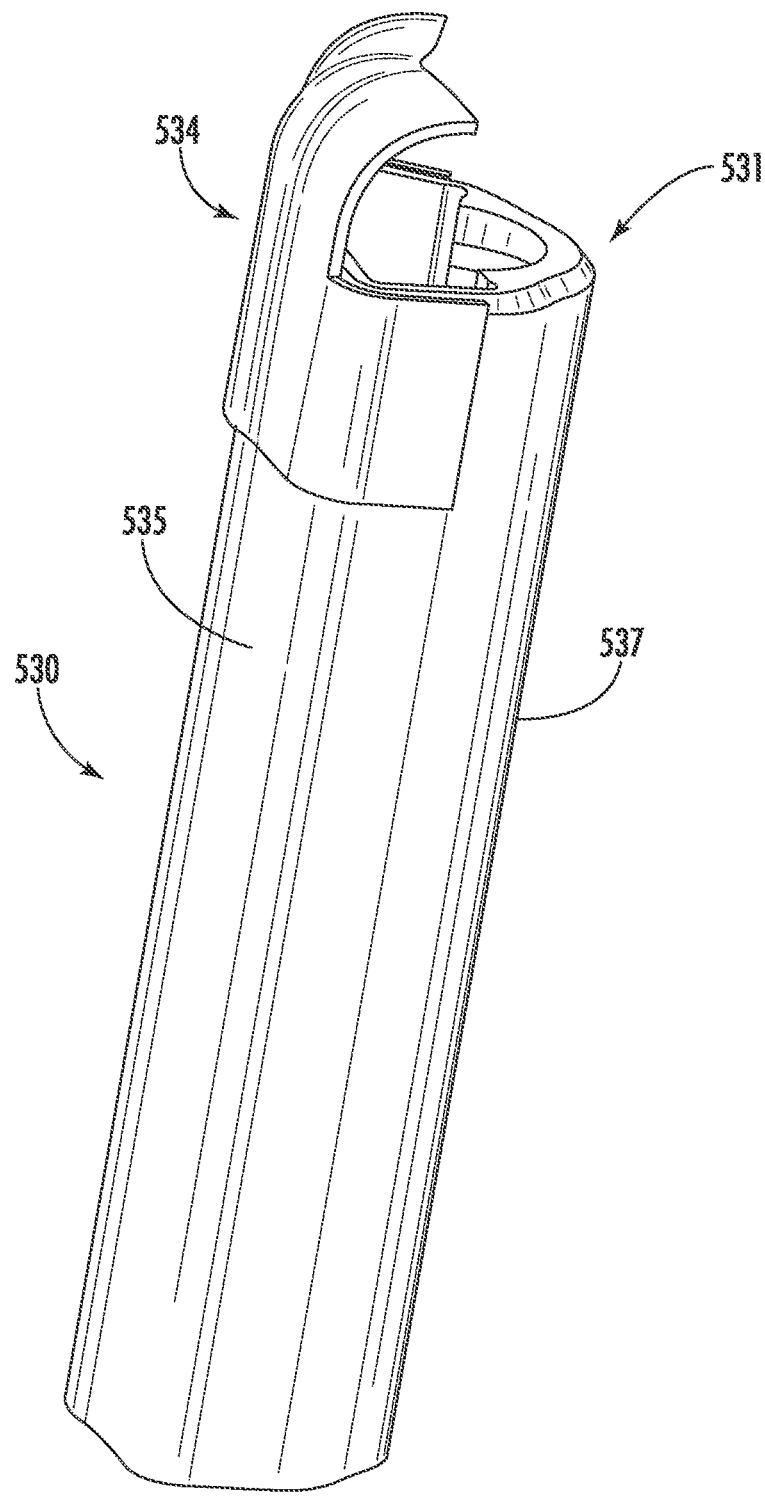
FIG. 10 is a front perspective view of an example of an embodiment of an atraumatic structure formed in accordance with various principles of the present disclosure.

In the embodiment of FIG. 10, a slider 530 has a shield 534 provided at a proximal end 531 thereof, extending from the outer surface 535 towards the inner surface 537 of the slider 530. The shield 534 extends over the open proximal end 531 of the slider 530 to shield the surrounding tissue from the proximal end 141 of a slider screw 140 within the slider 530, particularly the latch coupler 124 of the slider screw 140. The shield 534 may be machined from the material of the slider 530 or formed of a similar material as the slider 530 and added thereto (e.g., by welding or snapping into place such as with interlocking parts or a friction or interference fit). Alternatively, the shield 534 may be formed of a flexible, resilient material (e.g., silicone) covering the proximal end 141 of the slider screw 140 and movable out of the way for access to the latch coupler 124 by a latch 1044 of a delivery/deployment device (such as the latch and delivery/deployment device illustrated in FIG. 9) and an actuator 1040. In another alternative configuration, as illustrated in FIG. 11, a shield 534' similar to the shield of the embodiment of FIG. 10 may be provided with a slit 533' or other space in the shield 534' to form a pair of spaced apart shields 534a', 534b' with the slit 533' therebetween facilitating access to the latch coupler 144 of a slider screw 140 within the slider 530 and/or to facilitate flexibility of the shield 534'.

Figure 11:
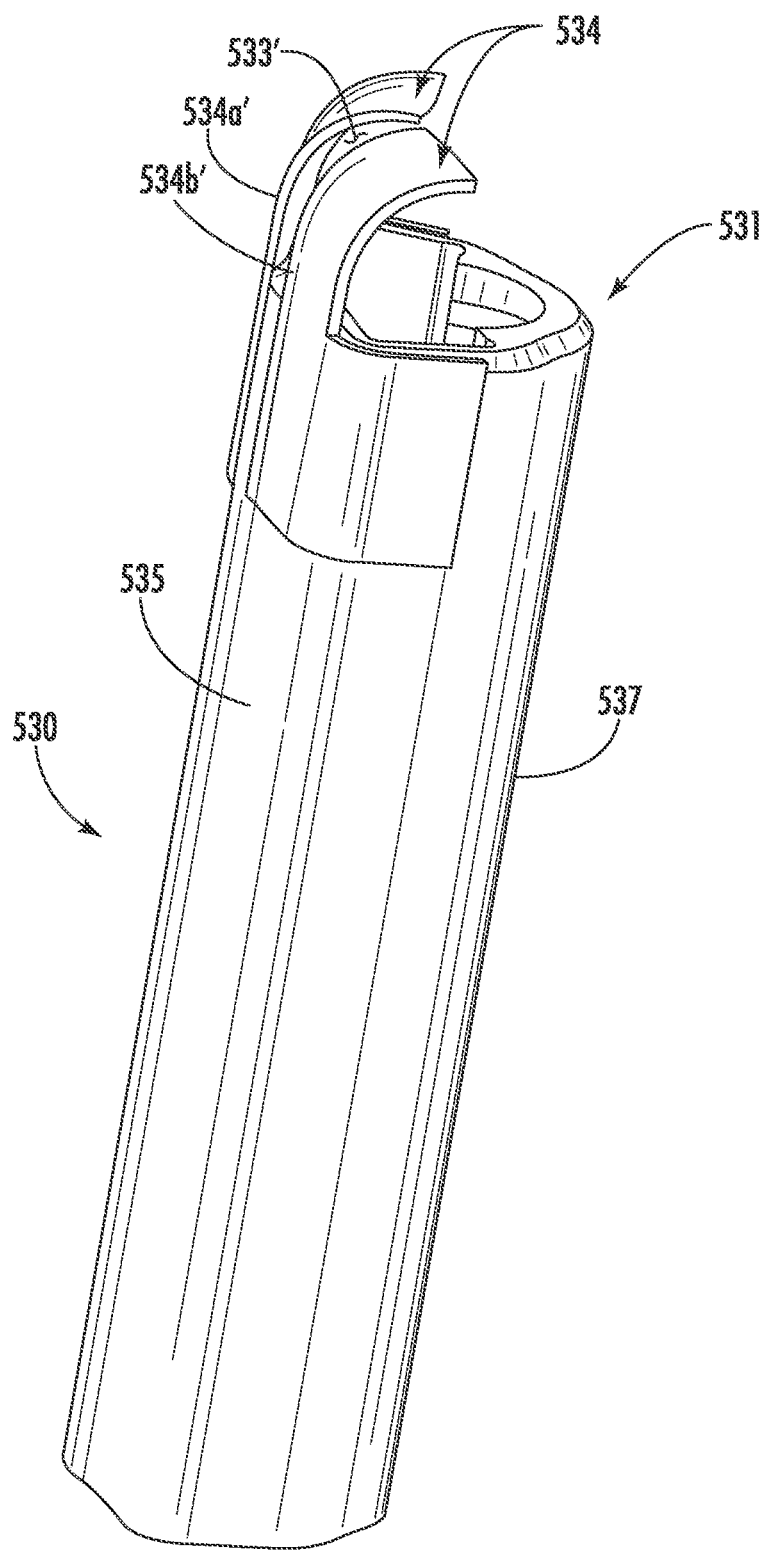
FIG. 11 is a front perspective view of an example of an embodiment of an atraumatic structure formed in accordance with various principles of the present disclosure.
Figure 12:
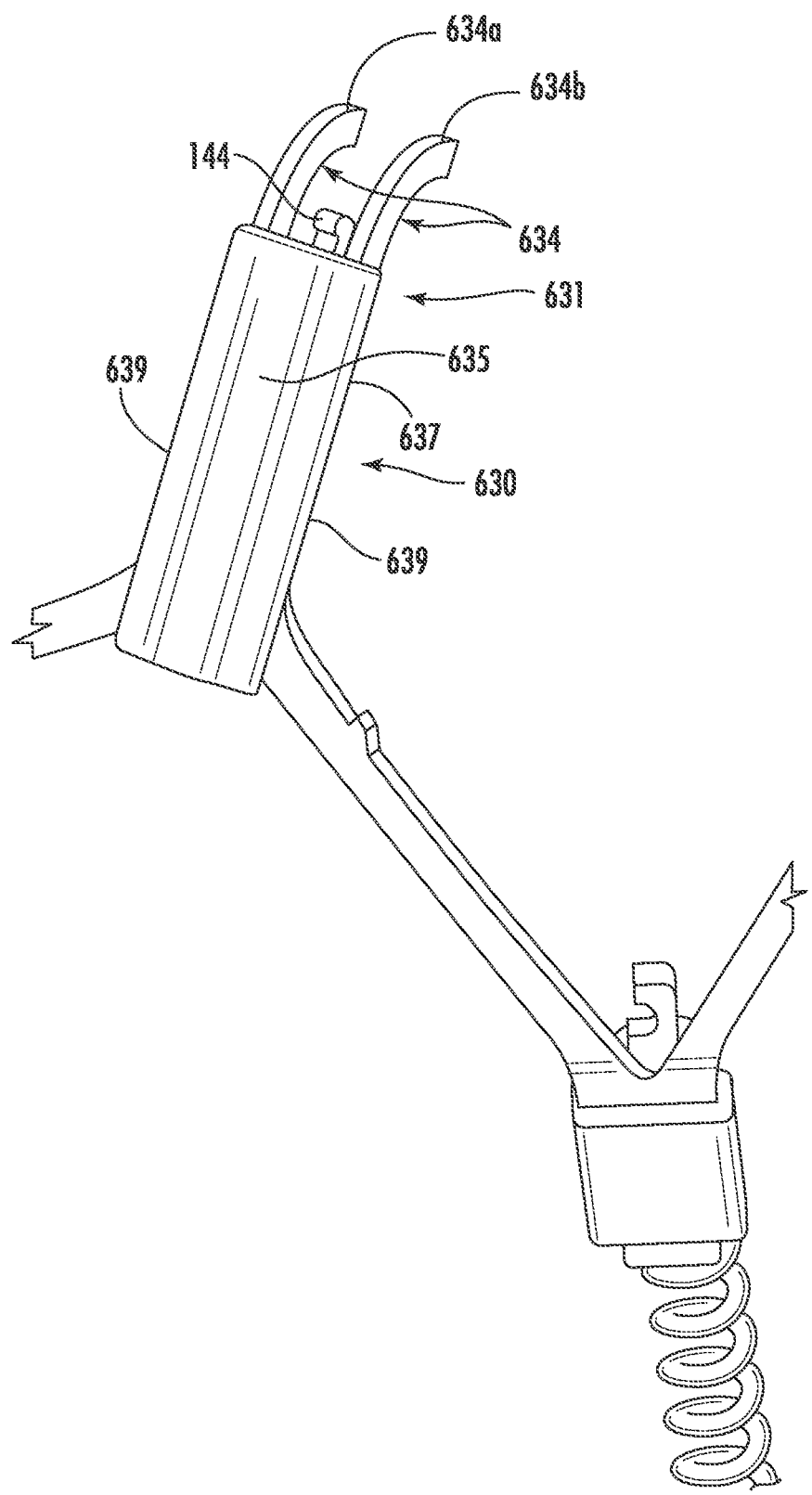
FIG. 12 is a front perspective view of an example of an embodiment of an atraumatic structure formed in accordance with various principles of the present disclosure on a perspective partial view of an example of an implantable device.

In the embodiment illustrated in FIG. 12, a shield 634 is provided in a similar manner as the shield 534, 534' illustrated in FIGS. 10 and 11. However, the thickness in a front to back direction (in a direction from the front outer surface 635 to the back interior surface 637) is thicker than the shield 534, 534' illustrated in FIGS. 10 and 11. Additionally or alternatively, a larger space 533' may be provided in the shield 634 than in the shield 534' illustrated in FIG. 11, leaving a pair of curved elements 634a, 634b (which may be referenced as horns or fingers or the like, without intent to limit) each with a width (in a direction extending between the side surfaces 639) smaller than the width of the shield portions 534a', 534b' illustrated in FIG. 11. The space 633 between the curved elements 634a, 634b may be sufficiently large (and/or the placement of the curved elements 634a, 634b close enough to the sides 639 of the slider 630) to allow a flexible elongate member 1042 and an associated actuator 1040 of a delivery/deployment device (such as the latch and delivery/deployment device illustrated in FIG. 9) to extend therebetween to access and to engage a latch coupler 424 of a slider screw 140 within the slider 630.

Figure 13:
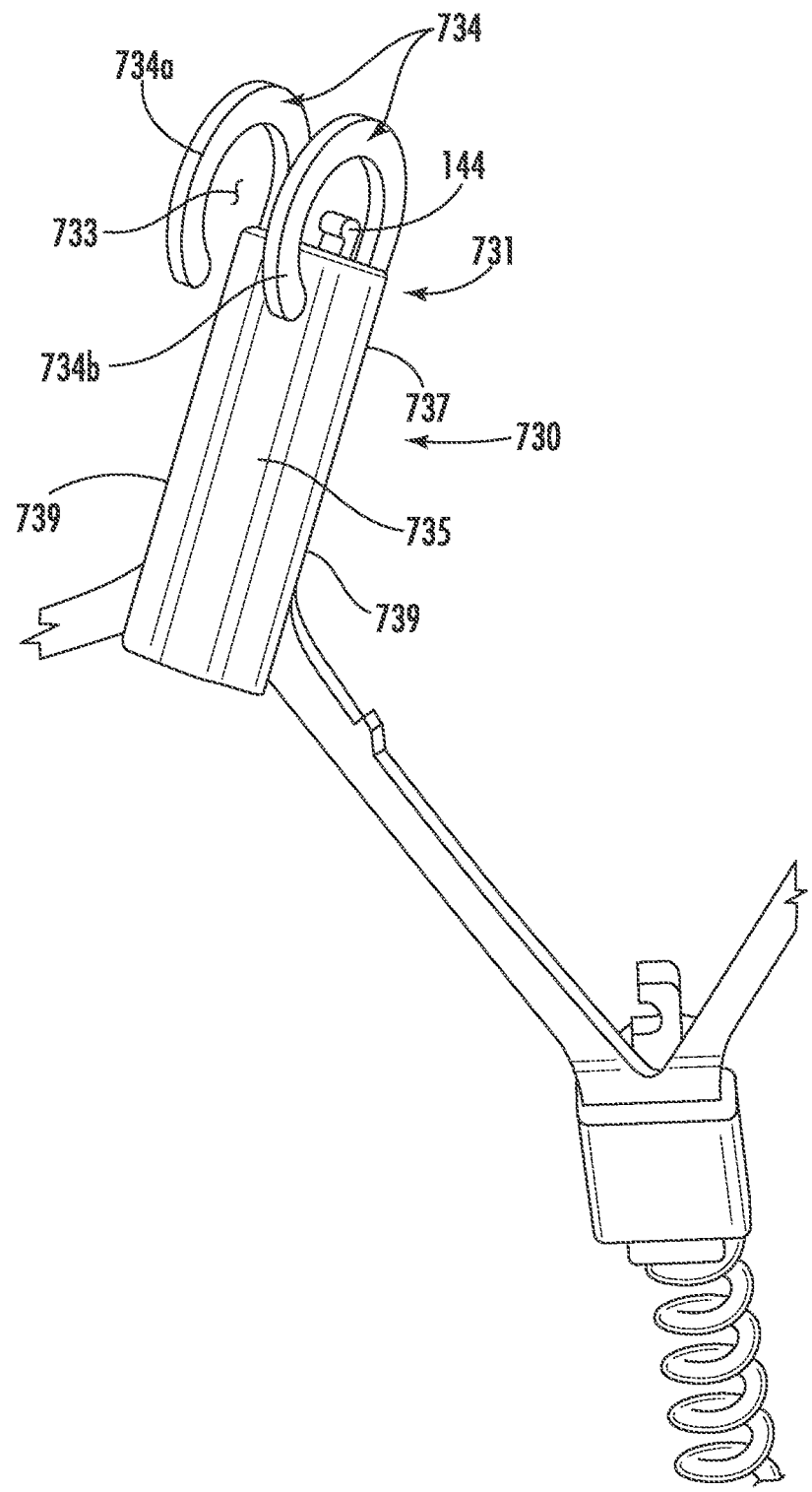
FIG. 13 is a front perspective view of an example of an embodiment of an atraumatic structure formed in accordance with various principles of the present disclosure on a perspective partial view of an example of an implantable device.

In another embodiment of a slider 730, as illustrated in FIG. 13, a shield 734 may be provided extending outwardly from the outer surface 735 of the slider 730 (and towards the exterior 115 of the frame 110 illustrated in FIG. 1). Like the shield 634 of the embodiment of FIG. 12, the shield 734 of the embodiment of FIG. 13 may form a pair of horns 734a, 734b sufficiently spaced apart (and/or the placed close enough to the sides 739 of the slider 730) to allow a flexible elongate member 1042 and an associated actuator 1040 of a delivery/deployment device (such as the latch and delivery/ deployment device illustrated in FIG. 9) to extend therethrough to access and to engage a latch coupler 144 of a slider screw 140 within the slider 630.

Figure 14:
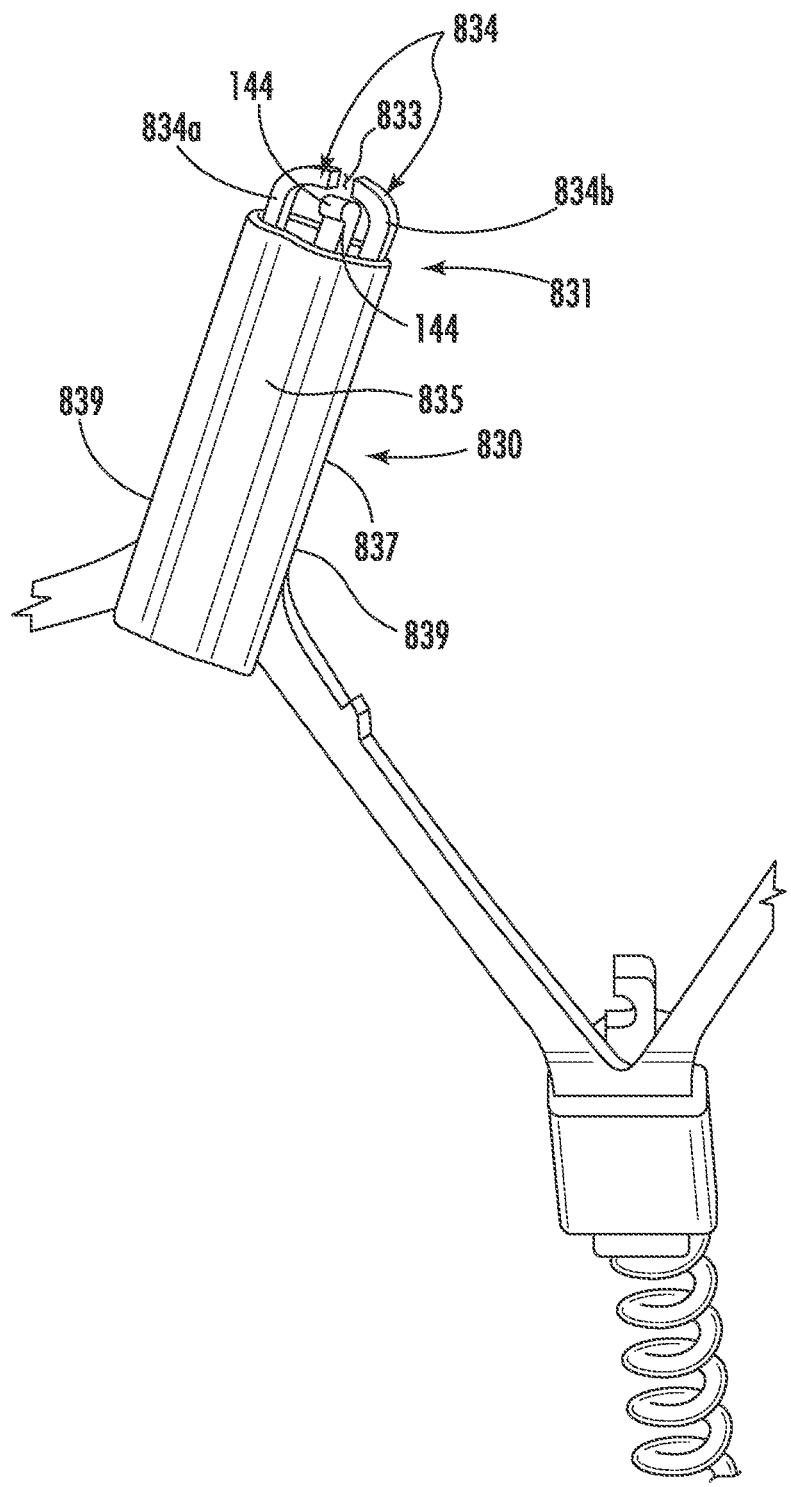
FIG. 14 is a front perspective view of an example of an embodiment of an atraumatic structure formed in accordance with various principles of the present disclosure on a perspective partial view of an example of an implantable device.

Instead of a slider having a shield with curved elements extending in a direction between the front and back of the slider (as in the embodiments of FIGS. 10-13), a slider 830 may be provided with a shield 834 having first and second inwardly extending curved elements 834a, 834b, as illustrated in FIG. 14. The curved elements 834a, 834b may be coupled adjacent to the side surfaces 839 of the slider 830 and extend proximally and inwardly towards each other. The curved elements 834a, 834b may be substantially equidistantly spaced between the front exterior surface 835 and the back interior surface 839 of the slider 830. However, other positions are within the scope and spirit of the present disclosure. A space 833 may be provided between the proximal ends of the curved elements 834a, 834b to allow a flexible elongate member 1042 and an associated actuator 1040 of a delivery/deployment device (such as the latch and delivery/deployment device illustrated in FIG. 9) to extend therethrough to access and to engage a latch coupler 144 of a slider screw 140 within the slider 830.

Figure 15:
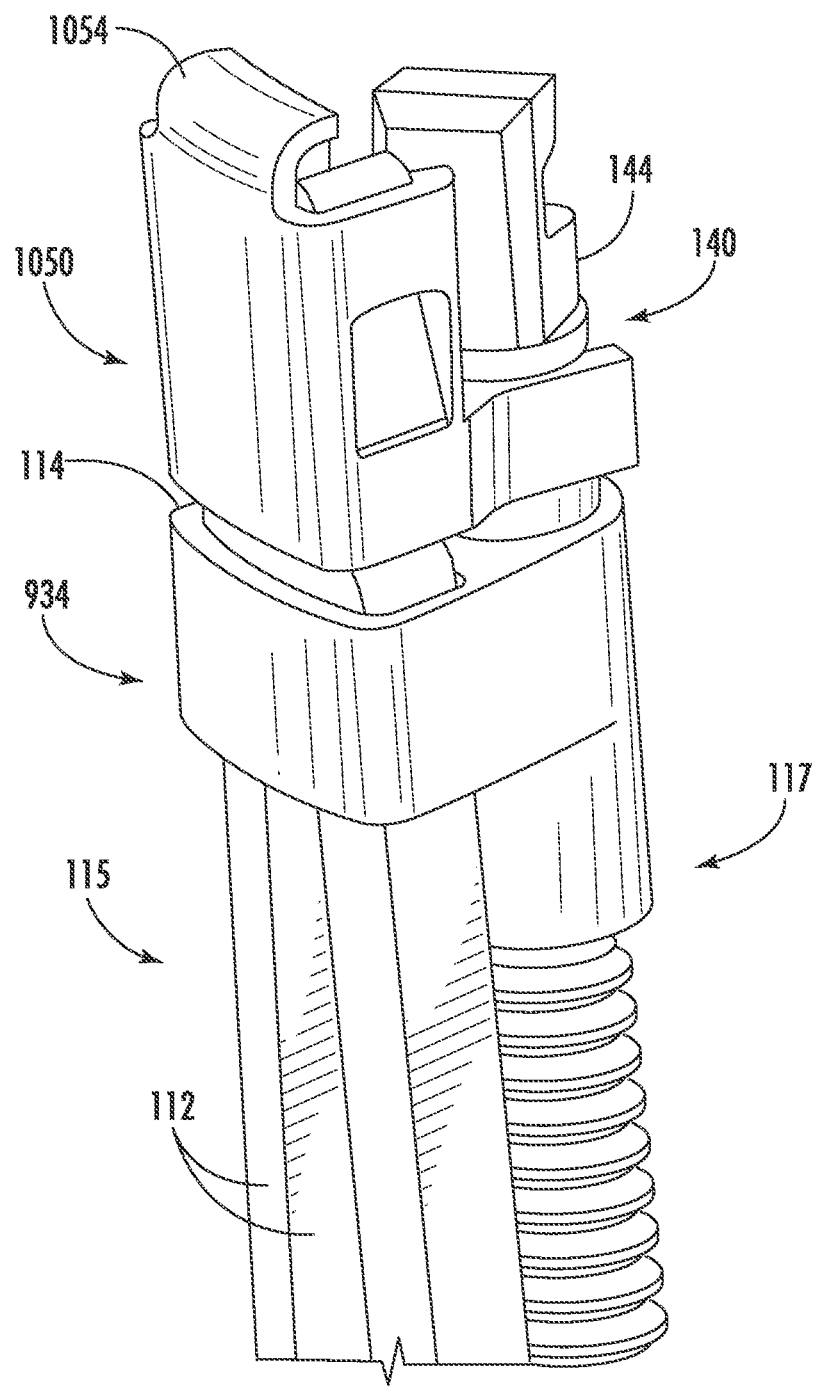
FIG. 15 is a front perspective view of an example of an embodiment of an atraumatic structure formed in accordance with various principles of the present disclosure.
Figure 16:
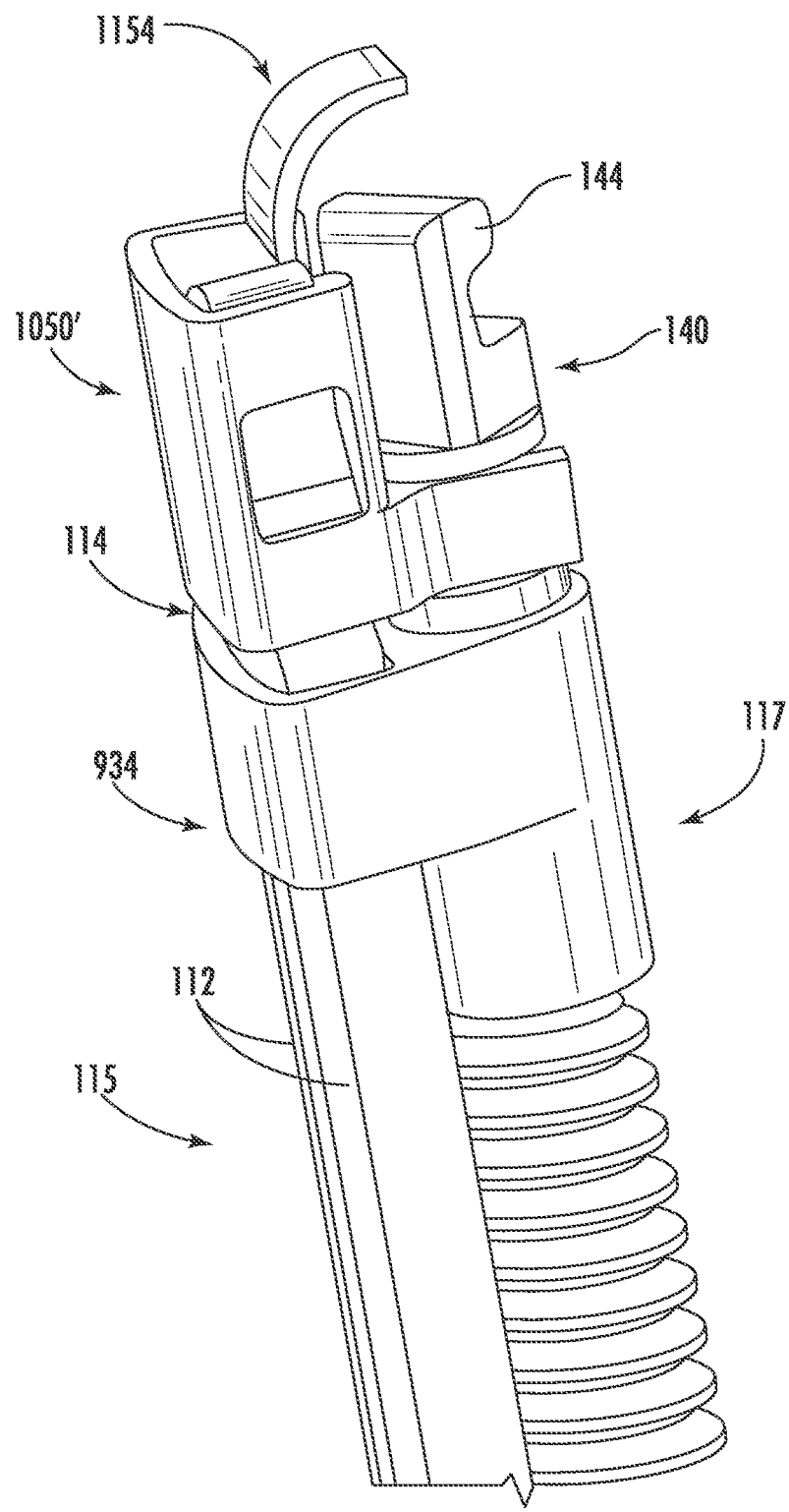
FIG. 16 is a front perspective view of an example of an embodiment of an atraumatic structure formed in accordance with various principles of the present disclosure.

As illustrated in FIGS. 15 and 16, in some embodiments, a slider 934 may be coupled below the proximal end of a proximal apex 114 of a frame 110 (illustrated in full in FIG. 1). In such case, a shield attachment 1050, 1050' may be mounted on the proximal apex 114 of the frame 110, with a curved shield 1054, 1054' extending from the exterior 115 of the frame 110 towards the interior 117 of the frame 110 to extend over the latch coupler 144 of the anchor 120. In the embodiment illustrated in FIG. 15, a curved shield 1054 extends from an exterior side of the proximal apex 114 inwardly, whereas in the embodiment of FIG. 16, a curved shield 1054' extends from an interior side of the proximal apex 114 inwardly over the latch coupler 144. It will be appreciated that the length of the curved shield 1054, 1054' may be varied to provide the desired shielding of the latch coupler 144 from contacting tissue surrounding the implantable device 100. If desired, the curved shield 1054, 1054' may be formed of a substantially resilient and flexible material to be flexed out of the way above a latch coupler 144 to facilitate access to the latch coupler 144.

Principles of the present disclosure have been described as applied to devices designed to reconfigure and/or repair cardiac valves (e.g., mitral and tricuspid valves), such as to treat valvular regurgitation. However, the principles of the present disclosure can also be applied to other cardiovascular devices, such as devices with two or more struts that are cinched together during implantation, and/or other devices presenting a potential risk of tissue damage. Furthermore, it will be appreciated that various other implants may similarly benefit from the structures and features disclosed herein.

Various structures and features of the embodiments described herein and illustrated in the figures have several separate and independent unique benefits. Therefore, the various structures and features described herein need not all be present in order to achieve at least some of the desired characteristics and/or benefits described herein. Moreover, the various features described herein may be used singly or in any combination. It will be appreciated that various features described with respect to one embodiment may be applied to another embodiment, whether or not explicitly indicated. Thus, it should be understood that one or more of the features described with reference to one embodiment can be combined with one or more of the features of any of the other embodiments described herein. That is, any of the features described herein can be mixed and matched to create hybrid designs, and such hybrid designs are within the scope of the present disclosure. Therefore, the present invention is not limited to only the embodiments specifically described herein. The above descriptions are of illustrative examples of embodiments only, and are not intended as limiting the broader aspects of the present disclosure.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. as used herein, a "free end" of an element is a terminal end at which such element does not extend beyond. Identification references (e.g., primary, secondary, first, second, third, fourth, etc.) are not intended to connote importance or priority, but are used to distinguish one feature from another. The following claims are hereby incorporated into this Detailed Description by this reference, with each claim standing on its own as a separate embodiment of the present disclosure. Reference signs in the claims are provided merely as a clarifying example and shall not be construed as limiting the scope of the claims in any way.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "the", "first", "second", etc., do not preclude a plurality. Reference signs in the claims are provided merely as a clarifying example and shall not be construed as limiting the scope of the claims in any way.

What is claimed is:

1. An implantable device configured to be implanted in a patient's heart, the implantable device comprising a frame shiftable between a collapsed configuration and an expanded configuration, and extending along a longitudinal axis between a distal end and a proximal end, wherein:
   the distal end of the frame is configured to be secured to tissue at an implant site within the patient's heart
   the proximal end of the frame extends away from the distal end; and
   the frame further comprises a curved structure positioned over the proximal end of the frame and curved about an axis transverse to the longitudinal axis of the frame to shielding the proximal end of the frame from heart tissue surrounding the implant site.

2. The implantable device of claim 1, wherein:
   the frame comprises a plurality of struts forming proximal apices along the proximal end of the frame; and
   the curved structure shields at least one proximal apex.

3. The implantable device of claim 2 further comprising a slider positioned over the at least one proximal apex, wherein the curved structure is on the slider.

4. The implantable device of claim 1, wherein the curved structure is a rounded proximal end of a slider positioned over a portion of the frame to be slidable with respect to the frame along the longitudinal axis thereof.

5. The implantable device as in claim 3, further comprising a slider screw engaging the slider to move the slider with respect to the struts to shift the frame between the collapsed configuration and the expanded configuration, wherein the slider screw has a latch coupler on a proximal end thereof, and the curved structure shields the latch coupler.

6. The implantable device of claim 3, wherein the curved structure comprises a rounded cap.

7. The implantable device as in claim 3, wherein the curved structure is a shield mounted on the at least one proximal apex.

8. An implantable device configured to be implanted in a patient's heart, the implantable device comprising:
a frame having an outer side and an inner side relative to a frame axis, a distal end configured to be secured to cardiac tissue at an implant site within the patient's heart, and a proximal end configured to be coupled with a delivery deployment device;
at least one latch coupler extending proximally from a proximal end of the frame and configured to be coupled with a delivery deployment device; and
a curved structure, curved in a direction between the outer side and the inner side of the frame, shielding the at least one latch coupler from cardiac tissue surrounding the implant site within the patient's heart.

9. The implantable device of claim 8, further comprising:
a slider mounted on a portion of the frame; and
a slider screw engaging the slider to actuate the slider to shift the frame between a collapsed configuration and an expanded configuration;
wherein the latch coupler is positioned on a proximal end of the slider screw.

10. The implantable device of claim 9, wherein the curved structure is a proximal end of the slider curved along an outer surface thereof and extending proximally towards a proximal end of the frame.

11. The implantable device of claim 9, wherein the curved structure is a proximal end of the slider curved from a side thereof extending transverse to the outer side of the frame, and extending towards a proximal end of the frame.

12. The implantable device of claim 8, further comprising at least one anchor on the distal end of the frame, wherein the anchor is configured to secure the implantable device to cardiac tissue, and the latch coupler is positioned on a proximal end of the anchor.

13. The implantable device of claim 8, wherein the curved structure is a curved shield extending from the outer side of the frame towards the inner side of the frame to extend proximally over the at least one latch coupler.

14. The implantable device of claim 13, further comprising:
a slider mounted on a portion of the frame; and
a slider screw engaging the slider to actuate the slider to shift the frame between a collapsed configuration and an expanded configuration;
wherein:
the latch coupler is positioned on a proximal end of the slider screw; and
the shield extends from the slider proximally over the latch coupler.

15. The implantable device of claim 13, further comprising:
a slider mounted on a portion of the frame; and
a slider screw engaging the slider to actuate the slider to shift the frame between a collapsed configuration and an expanded configuration;
wherein:
the latch coupler is positioned on a proximal end of the slider screw; and
the shield is mounted on the frame proximal to the slider and slider screw and extends proximally over the latch coupler.

16. The implantable device of claim 13, wherein the curved shield comprises first and second curved elements on either side of the latch coupler to allow access to the latch coupler by a delivery deployment device therebetween.

17. The implantable device of claim 13, wherein the curved shield is flexible to allow access to the latch coupler by a delivery deployment device therebetween.

18. The implantable device of claim 8, wherein the curved structure comprises a rounded cap extending over the latch coupler.

19. An implantable annuloplasty device having a distal end configured to be implanted around a cardiac valve annulus and a proximal end configured to be coupled to a delivery deployment device, the implantable annuloplasty device comprising:
a frame having an inner circumference and an outer circumference and shiftable between a collapsed configuration and an expanded configuration to reconfigure the cardiac valve annulus; and
a curved structure, curved in a radial direction between the inner circumference and the outer circumference, shielding the proximal end of the implantable annuloplasty device from the cardiac wall surrounding the cardiac valve annulus.

20. The implantable annuloplasty device of claim 19, further comprising:
a slider mounted on a portion of the frame; and
a slider screw engaging the slider to actuate the slider to shift the frame between the collapsed configuration and the expanded configuration;
wherein:
the slider screw has a latch coupler on a proximal end thereof configured to be coupled with a latch on a delivery deployment device; and
the curved structure curves proximally over the latch coupler to shield the latch coupler from the cardiac wall surrounding the cardiac valve annulus.

* * * * *